United States Patent
Carta

(10) Patent No.: US 11,272,681 B2
(45) Date of Patent: Mar. 15, 2022

(54) NETWORK OF IOT SENSORS FOR MONITORING HARMFUL GAS IN ANIMAL STABLES

(71) Applicant: CYNOMYS S.R.L., Genoa (IT)

(72) Inventor: Enrico Carta, Isola del Cantone (IT)

(73) Assignee: CYNOMYS S.R.L., Genoa (IT)

( * ) Notice: Subject to any disclaimer, the term of this patent is extended or adjusted under 35 U.S.C. 154(b) by 116 days.

(21) Appl. No.: 16/619,110

(22) PCT Filed: Jun. 4, 2018

(86) PCT No.: PCT/IT2018/050100
§ 371 (c)(1),
(2) Date: Dec. 4, 2019

(87) PCT Pub. No.: WO2018/225107
PCT Pub. Date: Dec. 13, 2018

(65) Prior Publication Data
US 2020/0093088 A1    Mar. 26, 2020

(30) Foreign Application Priority Data

Jun. 5, 2017 (IT) .......................... 102017000061107

(51) Int. Cl.
*A01K 1/00* (2006.01)
*G06K 9/00* (2022.01)
(Continued)

(52) U.S. Cl.
CPC ........ *A01K 1/0047* (2013.01); *G06K 9/00362* (2013.01); *G16Y 10/05* (2020.01);
(Continued)

(58) Field of Classification Search
CPC ...... A01K 1/0047; A01K 29/00; G16Y 10/05; G08B 21/14; G08B 21/182; G01N 33/0063; H04Q 9/00; G06K 9/00362
See application file for complete search history.

(56) References Cited

U.S. PATENT DOCUMENTS

2006/0287842 A1* 12/2006 Kim ........................ G01H 9/004
702/183
2010/0306189 A1* 12/2010 Kim .................. G06F 16/24544
707/714
(Continued)

FOREIGN PATENT DOCUMENTS

GB          2537170        10/2016
WO         2014129966       8/2014

OTHER PUBLICATIONS

International Search Report and Written Opinion dated Oct. 12, 2018 for PCT Patent No. PCT/IT2018/050100.

*Primary Examiner* — Ojiako K Nwugo
(74) *Attorney, Agent, or Firm* — Thomas | Horstemeyer, LLP

(57) ABSTRACT

The present disclosure relates to providing a continuous, autonomous monitoring system of environmental parameters, harmful gases and greenhouse gases in animal stables. A network of internet-of-things (IoT) sensors can be installed in a stable that produce alarm signals in case of danger or if predetermined threshold values are exceeded. The sensors work continuously and communicate through different wireless protocols with a dedicated cloud platform. The cloud platform stores the values received by the various sensor units and transmitted via dedicated monitoring devices and elaborates them applying data analysis processes.

20 Claims, 3 Drawing Sheets

(51) Int. Cl.
*H04Q 9/00* (2006.01)
*G16Y 10/05* (2020.01)
*G01N 33/00* (2006.01)
*G08B 21/14* (2006.01)
*G08B 21/18* (2006.01)
*A01K 29/00* (2006.01)

(52) U.S. Cl.
CPC .............. *H04Q 9/00* (2013.01); *A01K 29/00* (2013.01); *G01N 33/0063* (2013.01); *G08B 21/14* (2013.01); *G08B 21/182* (2013.01)

(56) References Cited

U.S. PATENT DOCUMENTS

| | | | |
|---|---|---|---|
| 2013/0156016 A1* | 6/2013 | Debnath | H04W 56/00 370/336 |
| 2013/0278427 A1* | 10/2013 | Setton | G08B 27/00 340/584 |
| 2015/0194039 A1* | 7/2015 | Martin | H04W 72/0453 340/632 |
| 2016/0061476 A1* | 3/2016 | Schultz | F24F 11/30 700/276 |
| 2016/0072891 A1* | 3/2016 | Joshi | G06Q 30/0631 370/254 |
| 2017/0086011 A1* | 3/2017 | Neves | H04B 1/3822 |
| 2017/0154509 A1* | 6/2017 | Prabhakar | G08B 21/16 |
| 2017/0370891 A1* | 12/2017 | Yoo | G01N 33/0044 |
| 2018/0231946 A1* | 8/2018 | Savo | G05B 19/4185 |
| 2018/0283148 A1* | 10/2018 | Ortiz | G05D 16/2026 |
| 2019/0035253 A1* | 1/2019 | Jones, II | G08B 21/14 |

\* cited by examiner

NETWORK OF IOT SENSORS FOR MONITORING HARMFUL GAS IN ANIMAL STABLES

CROSS-REFERENCE TO RELATED APPLICATIONS

This application is a § 371 national phase application of PCT/IT2018/050100 filed Jun. 4, 2018 entitled "NETWORK OF IOT SENSORS FOR MONITORING HARMFUL GAS IN ANIMAL STABLES," which claims the benefit of and priority to Italian Patent Application No. 102017000061107 filed Jun. 5, 2017, the contents of which being incorporated by reference in their entireties herein.

BACKGROUND

The agricultural and zootechnical activities emit pollutants that can impact on all the environmental sectors: air, water, soil, plants and animals. In particular, intensive livestock farms are a considerable source of irritating gases such as ammonia ($NH_3$) and hydrogen sulphide ($H_2S$), and greenhouse gases such as methane ($CH_4$), nitrous oxide ($N_2O$) and carbon dioxide ($CO_2$), believed to be the agents responsible for soil acidification and global warming (IPCC 2013, http://www.ipcc.ch/report/ar5/wg1/). It is known that more than 90% of ammonia released into the atmosphere derives from agriculture and it is also known that about 97% of agricultural emissions derive from animal husbandry and related activities; moreover 50% of these emissions are released by zootechnical structures intended as animal shelters and stored sewage. Ammonia ($NH_3$) is produced by the fermenting urea in animal dejections and is toxic at concentrations above 50 parts per million (from now on ppm). In closed environments such as barns, stalls and sheds for animal husbandry, its concentration can reach levels even higher than 60 ppm. Through a series of chemical reactions it can be transformed into nitrogen oxides (NOx) and contribute to the phenomenon of acid rain. Hydrogen sulphide ($H_2S$) in animal farms originates from the decomposition of animal dejections. Normally present in the atmosphere at concentrations between 0.11 and 0.33 ppb (parts per billion), in intensive farms it is found at concentrations lower than 2-3 ppm, but it can reach peaks of 80-800 ppm during the handling of slurry.

This acid has a toxic effect already at 50 ppm. Nitrous oxide ($N_2O$) and methane ($CH_4$) are other emissions typically produced by zootechnical sewage. The methane ($CH_4$) is one of the most significant greenhouse gases, having a specific impact 21 times higher than the carbon dioxide emitted by animals during respiration and fermentation of sewage. In zootechnics, the ability to control greenhouse gas emissions is often limited and difficult to manage. However, it is possible to intervene through targeted mitigation actions. Currently available techniques to reduce harmful gas emissions ($NH_3$, $H_2S$) in the animal stables are often easy to implement if performed promptly, such as the rapid removal of animal manure to an external tank; nonetheless, currently the concentration of gas in the stables is monitored manually and sporadically by operators who are in turn exposed to the gaseous emissions.

The automation and digitalization of the measurement system would allow farmers to implement targeted actions to mitigate emissions in a timely and efficient manner Such actions would have a beneficial effect on farmers as they would improve the productivity of the farm by limiting the risks to the health of operators and animals, reducing the energy consumption and, generally, lowering production costs.

An automated gas monitoring service would also provide farmers not only with data about harmful gases, but also with values useful to define their carbon footprint, i.e. the parameters that currently must be communicated to the competent authorities in accordance with the European directives on the mitigation of agricultural activities environmental impacts (protocol E-PRTR, http://www.eprtr.it/homepage.asp).

Monitoring the concentration of gas and environmental parameters in animal stables is still an open issue; to date there are no autonomous systems working continuously, 24/7, nor processes for data collection on harmful gas emissions (for humans, animals and environment) or environmental parameters such as temperature and humidity values in livestock farms allowing to analyse and return such data, processed, to the end user. Moreover, there are no integrated sensor systems to warn in real time if significant and predetermined threshold values of the above mentioned chemical and physical parameters are exceeded, thus putting at risk the welfare of the animals and operators.

Recently, wireless systems have been introduced (Hong et al., CN105608876) to deal with the problem of the detection of limited and sporadic environmental data (temperature and humidity) and the measurement of $NH_3$ in the stables. However, these solutions do not allow the measurement of $H_2S$ or greenhouse gases or the other parameters necessary to guarantee an optimal environment for animal breeding, for the health of the operator in the stables and to obtain maximum production efficiency. Furthermore, these solutions do not provide real-time alerting services, nor services for the analysis and return of data useful for environmental parameters monitoring and for the prevention, or the subsequent data visualisation via web applications. Moreover, they do not guarantee the safety of the environmental monitoring through storage systems on remote servers and not on site.

In addition to the patent mentioned before, there are other environmental monitoring systems through IoT networks that are based on an architecture made up of sensors distributed in different areas of the premises to be monitored that communicate with a single monitoring device responsible for transmitting data to a remote platform (GB 2537170 A, WO 2014/129966 A1, CN105608876). This bottleneck structure implies a complete loss of the collected data should the monitoring device communicating with the cloud stop working. The damage resulting from this weakness in the system design is potentially enormous for a production process that requires constant control as it happens with animal breeding.

TECHNICAL FIELD

The proposed system aims to overcome the technical problems mentioned above. This objective is achieved by a series of independent and autonomous monitoring devices, each one communicating directly with a cloud platform and containing appropriate sensors for monitoring the area of interest. This structure is designed to maintain the functionality of the system even if a monitoring device should have a malfunction.

Moreover, compared to the existing solutions, which do not allow flexibility in the choice of the used sensors, the solution of this patent allows the integration of up to 24 sensors inside a single monitoring device and the possibility to quickly replace them if needed thanks to a connection between the sensors and the shield of the monitoring device via removable and non-welded sockets.

The purpose of the present invention is to provide the stables of livestock farms with a monitoring system for harmful gases, greenhouse gases and environmental parameters which is currently not available on the market as an automated tool, not depending on the operator's action.

BRIEF SUMMARY OF INVENTION

The proposed system allows to: monitor harmful gases for humans and animals in the stables; monitor the chemical-physical environmental parameters necessary to ensure the optimal growth of the animals; ensure the recording and storage on a cloud platform of physical and chemical data recorded in the stables; analyse and process the data collected by applying algorithms and machine learning processes appropriate for each type of data; make the data available to the end user in real time through web applications usable via smart devices such as tablets, smartphones, PCs and functionally equivalent devices.

BRIEF DESCRIPTION OF THE DRAWINGS

The features and advantages of the proposed technical solution will be evident in the following description of a preferred but not exclusive embodiment represented, but not limited to, the 3 attached tables of drawings in which.

DETAILED DESCRIPTION

Figure 1:
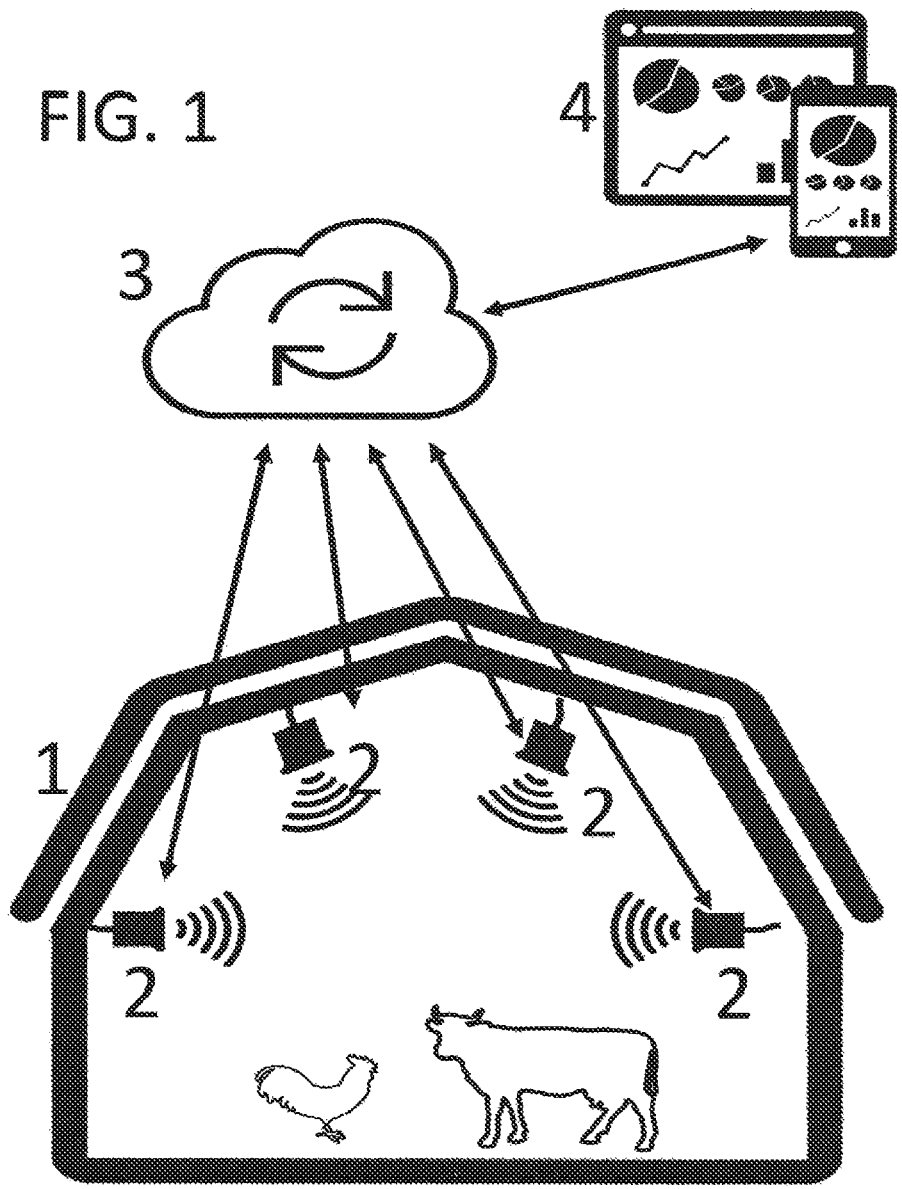
FIG. 1 shows a general scheme of the integrated system for monitoring gas and environmental parameters in a stable through a series of independent and autonomous monitoring devices hosting environmental sensors. Such devices are wirelessly connected to a cloud platform that returns the recorded data on a dashboard that can be accessed by smart mobile devices.
Figure 2:
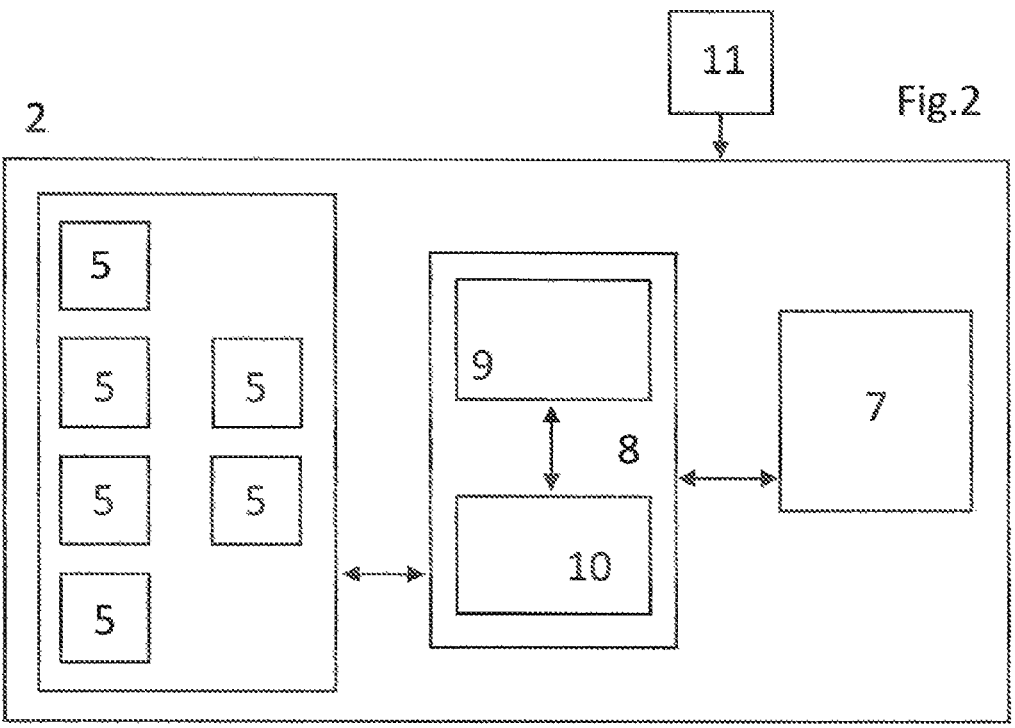
FIG. 2 shows a diagram of the mainboard characterizing each monitoring device and allowing data collection and communication with the cloud platform.
Figure 3:
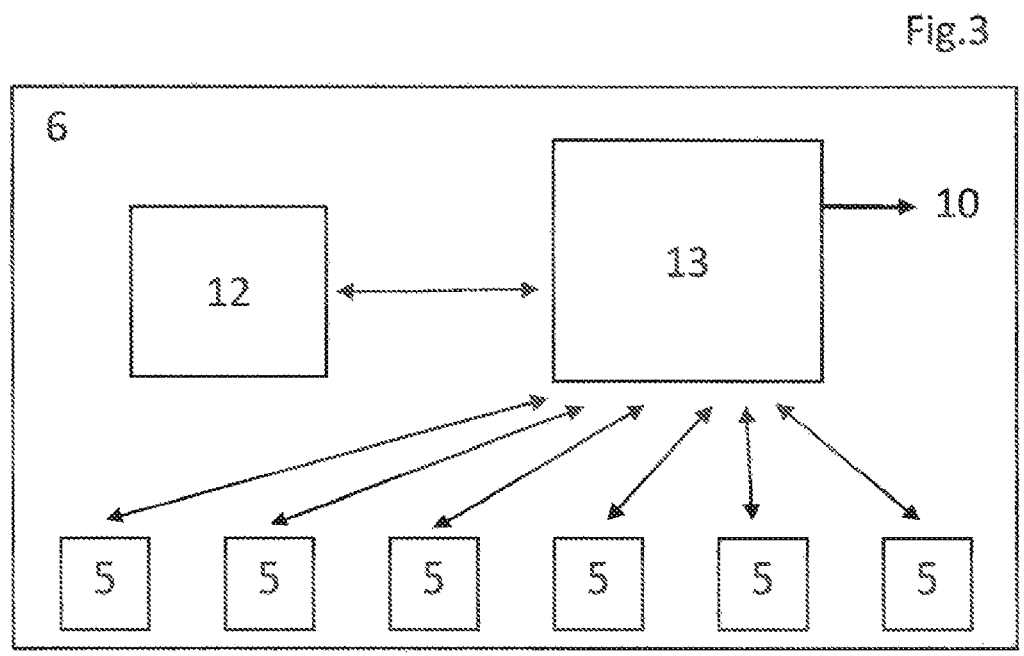
FIG. 3 shows a diagram of the shield inside each monitoring device allowing connection of one or more environmental sensors.
Figure 4:
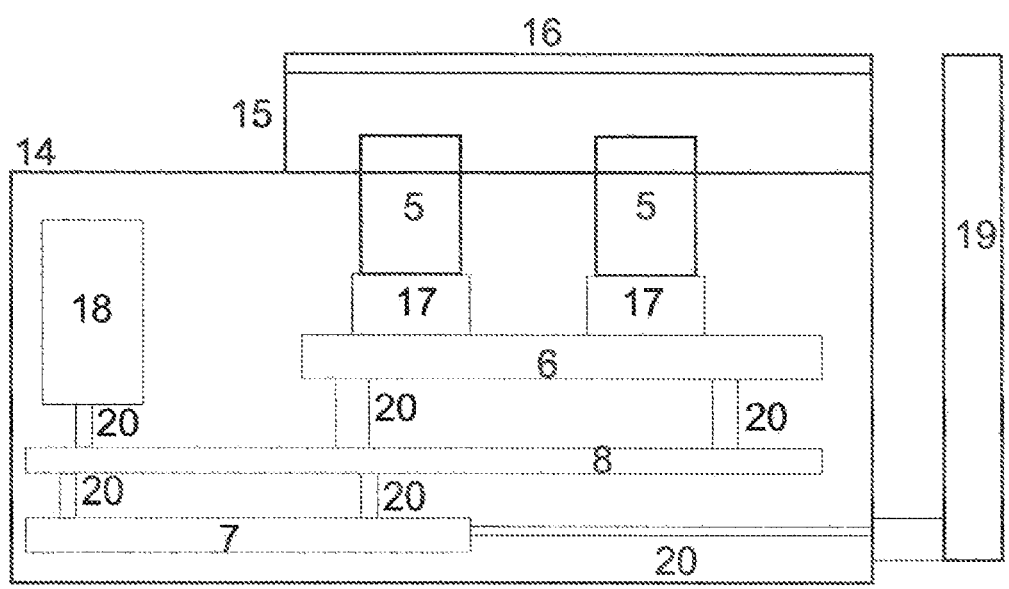
FIG. 4 shows a structural scheme of the and its components displayed as a cross-section.

According to the proposed solution, an integrated system for monitoring gases and environmental parameters in animal farms consists of a series of monitoring devices (2) whose number varies depending on the size of the stables to be monitored (1) and on the relative subdivision of the premises. These monitoring devices (2), powered by the electric network or by a photovoltaic panel with buffer battery (11), transmit the data collected by sensors (5) in wireless mode and via a communication module (7) to a software platform hosted on remote servers cloud (3). Through this system the parameters related to ammonia, methane, carbon dioxide, hydrogen sulphide, temperature, humidity, brightness, dust, noise, air velocity, electrical consumption and water consumption detected in the farms are decrypted and processed according to specific algorithms such as predictive models and machine learning techniques for the calibration of nowcasting and forecasting models that predict the behaviour over the medium and long term of the parameters detected in the farm and such information is made available to the farmer through a tool for the preventive maintenance of their farm. This tool sends directly to the farmer not only information, but also suggestions for the preventive maintenance of their farm, where preventive maintenance is intended as a series of actions that modify the physical-chemical conditions of the stables before critical values harmful for the production are reached. These medium and long-term predictions are presented as single or multi-parametric graphs vs time (for example the concentration of ammonia in the week, month or quarter) or as so-called compliance indices, i.e. values that farmers are legally required to observe (for example, maximum annual $CO_2$ emission values). Data relating to ammonia, methane, carbon dioxide, hydrogen sulphide, temperature, humidity, brightness, dust, noise, air velocity, electrical consumption and water consumption are made available on a dashboard (4) usable via PC/smartphone/tablet or functionally equivalent devices. The dashboard can be customized according to the needs of the end user and displays all or part of the detected parameters, it shows the pre and post-processing data; it provides a quick and immediate summary of the data collected in the stable, for example by summarizing them in green icons (normal values), yellow (values close to the damage threshold parameters), red (values beyond the damage threshold parameters). The end-user/farmer or other users can set autonomously the critical values that will trigger an alarm in real time.

The monitoring device (2) is characterized by a casing/box of variable dimensions and is characterized by a cover (15) adapted to an application requirement (different type and number of sensors compared to those mentioned above). This box/container (14) and the cover in its basic shape (15) can be made, for example, in ABS. In the basic cover there is a window covered by an impermeable porous membrane (16) that allows the exchange of gas between the monitoring device and the external environment and protects the sensors from liquid jets or foreign bodies intrusions.

The monitoring device is equipped with an integrated DIN connection to the outer rear part, to increase ease of installation. It is also equipped with a lithium buffer battery (18) which guarantees the system operation in the event of voltage drops or power failure. Moreover, in this case, the monitoring device sends a power failure alert via a text message, email or social notification.

Inside the monitoring device there are two printed circuit boards (PCBs): a mainboard (8) with the central processing unit (CPU) of the monitoring device (10) resides and a shield (6) accommodating the sensors to detect the chemical-physical parameters of the animal stables. These sensors (5) are placed inside the monitoring device (2) or outside and are connected by cable. In both cases, the sensors are connected to the shield (6) through removable and non-welded sockets (17) that allow a quick replacement of the sensors in case of need. The sensors can also be connected to the monitoring device in wireless mode, without limitation of protocols, through technologies such as, for example, but not limited to, Bluetooth®, Zigbee®, WiFi®, or the equivalent.

On each monitoring device, a communication module (7) is installed, equipped with an antenna (19), that is chosen according to the place of installation of the integrated system, and is adaptable to different technological standards on the market in order to keep the monitoring device constantly connected. As a non-limiting example, various data transmission technologies such as ethernet, wifi, Zig-Bee, gsm (gprs/3 g/lte), lora, sigfox, and/or functionally equivalent solutions can be employed. The monitoring device, thanks to the chosen communication module, is able to send the collected data directly to the cloud through currently used protocols such as, but not limited to, MQTT or http request. Each monitoring device is characterized by total independence from the overall integrated system installed in the stable, so the loss of functionality of one monitoring device does not preclude the performance of the others, in order to limit the damage due to the loss of data of a single area of the farm. This is due to the presence within each monitoring device of the communication module described above.

Within the monitoring device, the PCBs, the communication module, the antenna and the backup battery are connected to each other (20).

The mainboard (8), hosting the CPU of the monitoring device (10), has 6 analog inputs and 12 digital inputs/outputs. Despite this limitation, up to 24 analog probes can be connected to the monitoring device through the use of the digital inputs/outputs as switches between one probe and the other.

To ensure that both of the PCBs, namely, the mainboard (8) and the shield (6), inside the monitoring device (2) and the communication module (7) are resistant to water and dust, they are immersed in an epoxy dielectric resin bath before connecting the sensors to achieve a high degree of protection.

The monitoring device (2) allows two-way communications with a PC/smartphone/tablet. From these devices one can, in addition to reading the parameters of the custom dashboard, interact punctually with the monitoring device (2) by controlling the digital outputs. Power relays can be connected to these outputs to manage, as a non-limiting example, the actuation of fans, the opening of gates, the switching on and off of lights, the switching on and off of a heating/air conditioning system, etc. These electromechanical actuators can also be programmed to be activated when pre-established values are reached.

In case of failure of the cloud platform (3), each single monitoring device is able to send alarm signals (email, sms, social notifications) autonomously after detecting the excess of predetermined threshold values. This function ensures the redundancy of the alert system.

The raw data coming from the sensors are normalized by an integrated circuit (13) on the shield, controlled by an oscillator (12), and are sent to the CPU on the mainboard (10) that, by running the software inserted on a memory (9), elaborates a string of encrypted data to be sent to the cloud platform (3) via a communication module (7).

In addition to the probes already mentioned for the development of the predictive model, it is possible to connect to the monitoring device up to a maximum number of 24 other sensors according to the monitoring needs of the livestock farm. Some possible, but non-limiting, examples of sensors that can be connected are sensors for presence, atmospheric pressure, level, weight and any sensor functional for the automation and control of a stable.

The proposed solution can be used effectively in both existing and new animal farming facilities.

The proposed solution results lean, but complete for an integrated service to monitor ammonia, methane, carbon dioxide and hydrogen sulphide emissions, and to measure environmental parameters such as temperature, humidity, brightness, dust, noise, air velocity, electricity consumption and water consumption in animal farms.

Compared to other known solutions, the described system provides a considerable improvement because:

The sensors are integrated within a small and totally independent monitoring device (no wiring, maximum ease of installation), inside which the probes are not welded on the motherboard. This ensures a quick and economical maintenance in case of malfunction due to the easy replacement of each single sensor;

The monitoring devices are autonomous and independent, and send data to a cloud platform without intermediary tools. In this way the loss of functionality of a monitoring device does not cause any operation problem to the others;

A GSM or Sigfox module is installed on each monitoring device to guarantee a connection in any geographical area;

Each sensor unit can connect up to 24 probes on a monitoring device that is designed to receive 6 analogue inputs. By taking advantage of the digital i/o of the motherboard it is possible to operate on a number of analogue outputs which is 4 times higher;

The monitoring devices permit bidirectional communications that allow the control of electromechanical actuators inside the stable (e.g. fan activation, gates opening). These actuators can also be programmed to be activated when pre-established values are reached;

The PCBs inside the monitoring device are highly resistant to allow their application in hostile environments such as stables: they are resistant to water and dust thanks to an epoxy dielectric resin bath which isolates them completely;

The integrated system is equipped with a redundant alert system: in case of failure of the cloud platform, each single monitoring device is able to send alarms (email, sms, social notifications) when predetermined threshold values are exceeded;

The presence of a buffer battery on each monitoring device ensures its functioning in the event of voltage drops or power failure.

The invention according to the proposed embodiment is easy to manufacture and has a limited cost thanks to the use of components that do not require external validation tests.

The invention can be made with technical equivalents, with materials or additional procedures suitable for the purpose and the application field.

As a non-limiting example, it should be noted that the selected sensors can be replaced with other, more efficient ones, present on the market provided that the main functions mentioned above are maintained, i.e. the measurement of temperature, humidity, ammonia, methane, carbon dioxide, hydrogen sulphide, brightness, dust, noise, air velocity, electrical consumption and water consumption. Furthermore, in order to keep the monitoring devices connected to the cloud platform constantly, new wireless data transmission protocols can be implemented. As these implementations change, it will be necessary to modify the detection probes or the communication modules, without however parting from the scope of the proposed solution.

The invention claimed is:

1. An automated system for real-time monitoring and control of harmful gases, greenhouse gases, and environmental parameters in animal stables, comprising:

a plurality of independent and autonomous monitoring devices, each of the plurality of monitoring devices being equipped with at least one sensor for detecting gases and environmental parameters, each of the plurality of monitoring devices being equipped with a central processing unit (CPU) for processing sensor data and a communication module for transmitting the sensor data to a remote platform, each of the plurality of monitoring devices being provided with means for connecting and controlling electromechanical actuators; and the remote platform comprising at least one hardware processor and being configured through execution of program instructions stored in memory to:
provide an internet-based dashboard accessible from a client device located remotely from the remote platform, the internet-based dashboard configured to display the sensor data detected by the at least one sensor and display at least one alarm signal when a predefined threshold associated with the sensor data is exceeded; and
perform data analysis and data processing based on at least one machine learning algorithm, the at least one machine learning algorithm configured to predict an evolution over medium and long term of the environmental parameters detected by the at least one sensor of the plurality of monitoring devices, and the evolution as predicted being accessible through the internet-based dashboard in a form of mono-parametric or multi-parametric graph or compliance indicator.

2. The system according to claim 1, wherein the communication module further comprises at least one module for transmitting data, alarm signals, and commands to the client device.

3. The system according to claim 2, wherein at least one alarm signal, in case of a malfunction, is sent directly to the client device in the form of an email, text message, or social media notification.

4. The system according to claim 1, wherein each of the plurality of monitoring devices are enclosed in a casing for protecting the at least one sensor, the casing comprising a cover having a window comprising a porous membrane, the porous membrane providing gas permeability and protection of the at least one sensor from liquid and foreign bodies intrusion.

5. The system according to claim 1, wherein each of the plurality of monitoring devices further comprises:
a mainboard hosting a memory unit and the central processing unit (CPU);
an antenna for remote wireless communication;
a buffer battery; and
a series of digital outputs for controlling the electromechanical actuators.

6. The system according to claim 1, wherein:
the at least one sensor for detecting gases and environmental parameters comprises a plurality of sensors;
at least one of the plurality of sensors is configured to detect at least one of: ammonia, methane, hydrogen sulphide, and carbon dioxide; and
at least one of the plurality of sensors is configured to detect at least one of: temperature, humidity, brightness, dust, noise, air speed, electricity consumption, and water.

7. The system according to claim 6, wherein at least one of the plurality of sensors is positioned outside the casing of a corresponding one of the plurality of monitoring devices and connected to the corresponding one of the plurality of monitoring devices in a wired or wireless mode of connection.

8. The system according to claim 1, wherein at least one of the plurality of monitoring devices is powered by a standard electric power supply or a photovoltaic panel.

9. The system according to claim 1, wherein at least one of the electromechanical actuators controls at least one of: fans, gates, lights, conditioning systems, and general devices for the automation of the stable.

10. The system according to claim 1, wherein the internet-based dashboard comprises:
an internet based tool for displaying data received from the plurality of monitoring devices;
an internet based tool for displaying pre- and post-processing data;
an internet based tool for displaying a system status and for reporting alarm signals; and
an internet based tool for setting threshold values for sensor data values and corresponding alarm signals.

11. A method for performing real-time monitoring and control of harmful gases, greenhouse gases, and environmental parameters in an animal stable, comprising:
providing a plurality of monitoring devices, each of the plurality of monitoring devices being independent autonomous, each of the plurality of monitoring devices comprising:
at least one sensor configured to detect gas or an environmental parameter and collect sensor data;
a central processing unit (CPU) for processing the sensor data; and
a communication module for transmitting the sensor data to a remote computing device, at least one of the plurality of monitoring devices being connected to and configured to control at least one electromechanical actuator;
providing, by the remote computing device, a network-based dashboard accessible by a client device located remotely from the remote computing device the network-based dashboard that displays the sensor data detected by the at least one sensor and displays at least one alarm signal when a predefined threshold associated with the sensor data is exceeded; and
performing, by the remote computing device, data analysis and data processing based on at least one machine learning algorithm, the at least one machine learning algorithm configured to predict an evolution over medium and long term of the environmental parameters detected by the at least one sensor of the plurality of monitoring devices, and the evolution as predicted being accessible through the network-based dashboard in a form of a mono-parametric or multi-parametric graph or compliance indicator.

12. The method according to claim 11, further comprising controlling the at least one electromechanical actuator to adjust at least one of: a fan, a gate, a light, and a conditioning system in the animal stable.

13. An automated system for real-time monitoring and control of harmful gases, greenhouse gases, and environmental parameters in animal stables, comprising:
a plurality of monitoring devices configured to operate independently and autonomously, each of the plurality of monitoring devices comprising at least one sensor configured to detect at least one gas and at least one environmental parameter as sensor data, a central processing unit (CPU) for processing the sensor data, a communication device for transmitting the sensor data remotely, and means for connecting and controlling at least one electromechanical actuator; and
at least one computing device comprising at least one hardware processor and memory having program instructions stored thereon that, when executed, direct the at least one computing device to provide a network-based dashboard accessible by a client device located remotely from the at least one computing device, the network-based dashboard configured to:

display the sensor data detected by the at least one sensor and display at least one alarm signal when a predefined threshold associated with the sensor data is exceeded, wherein the network-based dashboard displays data received from the plurality of monitoring devices; displays pre-processing and post-processing data; displays a system status and the at least one alarm signal; and sets threshold values for sensor data values and corresponding alarm signals.

14. The system according to claim 13, wherein the at least one computing device is further directed to send the at least one alarm signal, in case of a malfunction, to the client device in the form of an email, text message, or social media notification.

15. The system according to claim 13, wherein each of the plurality of monitoring devices are enclosed in a casing for protecting the at least one sensor, the casing comprising a cover having a window comprising a porous membrane, the porous membrane providing gas permeability and protection of the at least one sensor from liquid and foreign bodies intrusion.

16. The system according to claim 13, wherein each of the plurality of monitoring devices further comprises:
a mainboard hosting a memory unit and the central processing unit (CPU);
an antenna for remote wireless communication;
a buffer battery; and
at least one digital output for controlling the at least one electromechanical actuator, wherein the at least one electromechanical actuator controls at least one of: a fan, a gate, a light, a conditioning system, and a general device for automation of a stable.

17. The system according to claim 13, wherein:
the at least one sensor is a plurality of sensors;
at least one of the plurality of sensors is configured to detect at least one of: ammonia, methane, hydrogen sulphide, and carbon dioxide; and
at least one of the plurality of sensors is configured to detect at least one of: temperature, humidity, brightness, dust, noise, air speed, electricity consumption, and water.

18. The system according to claim 17, wherein at least one of the plurality of sensors is positioned outside the casing of a corresponding one of the plurality of monitoring devices and connected to the corresponding one of the plurality of monitoring devices in a wired or wireless mode of connection.

19. The system according to claim 13, wherein at least one of the plurality of monitoring devices is powered by a photovoltaic panel.

20. The system according to claim 13, wherein the network-based dashboard displays data received from the plurality of monitoring devices; displays pre- and post-processing data; displays a system status; reports alarm signals; and receives specifications of threshold values for sensor data values and corresponding alarm signals.

* * * * *